(12) United States Patent
Kikuchi et al.

(10) Patent No.: US 7,947,305 B2
(45) Date of Patent: May 24, 2011

(54) FAT-SOLUBLE DRUG COMPOSITION

(75) Inventors: Eichi Kikuchi, Chiba (JP); Seiko Kawada, Chiba (JP)

(73) Assignee: Riken Vitamin Co., Ltd., Tokyo (JP)

( * ) Notice: Subject to any disclaimer, the term of this patent is extended or adjusted under 35 U.S.C. 154(b) by 0 days.

(21) Appl. No.: 11/505,984

(22) Filed: Aug. 18, 2006

(65) Prior Publication Data
US 2007/0042036 A1  Feb. 22, 2007

(30) Foreign Application Priority Data

Aug. 19, 2005 (JP) ................................. 2005-238931

(51) Int. Cl.
*A61K 9/48* (2006.01)
(52) U.S. Cl. ...................................................... 424/452
(58) Field of Classification Search .................... 424/452
See application file for complete search history.

(56) References Cited

U.S. PATENT DOCUMENTS

| | | | |
|---|---|---|---|
| 3,865,603 A * | 2/1975 | Szymanski et al. ......... 106/145.1 |
| 4,689,235 A * | 8/1987 | Barnes et al. ................... 426/89 |
| 5,441,753 A * | 8/1995 | McGinley et al. .............. 426/96 |
| 5,645,856 A * | 7/1997 | Lacy et al. ..................... 424/455 |
| 5,756,543 A * | 5/1998 | Katsuragi et al. ............. 514/547 |
| 5,851,576 A | 12/1998 | Abboud |
| 5,891,925 A * | 4/1999 | Behr ............................... 424/9.1 |
| 6,048,562 A * | 4/2000 | Mandralis et al. ............. 426/573 |
| 6,652,880 B1 | 11/2003 | Aylwin et al. |
| 2002/0032171 A1 | 3/2002 | Chen et al. |
| 2003/0040492 A1* | 2/2003 | Haschke et al. ................ 514/23 |
| 2005/0244488 A1* | 11/2005 | Spilburg ....................... 424/450 |

FOREIGN PATENT DOCUMENTS

| | | | |
|---|---|---|---|
| JP | 58071876 A * | 4/1983 |
| JP | 61-12632 | 1/1986 |
| JP | 02113863 A * | 4/1990 |
| JP | 4-74339 | 11/1992 |
| JP | 2004-115544 | 4/2004 |
| JP | 2004-135681 | 5/2004 |
| WO | 00/59482 | 10/2000 |
| WO | 01/12155 | 2/2001 |

OTHER PUBLICATIONS www.octoplus.nl,Formulation Development of Poorly soluble Drugs, printed Apr. 17, 2008, http://ir.octoplus.nl/index.cfm/site/Octoplus/pageid/ODE2EFF8-D03E-C80E-104B0E3548A07E7D/index.cfm, 2 pages.*
www.nutritiondata.com,Milk, dry, nonfat, calcium reduced, printed Sep. 29, 2008 from http://www.nutritiondata.com/facts/dairy-and-egg-products/85/2?print=true, 3 pages.*
Remington's Pharmaceutical Sciences, Eighteenth Ed., 1990, pp. 1658-1665.*

* cited by examiner

*Primary Examiner* — Fereydoun Sajjadi
*Assistant Examiner* — Gigi Huang
(74) *Attorney, Agent, or Firm* — Wenderoth, Lind & Ponack, LLP.

(57) ABSTRACT

The present invention aims at providing a fat-soluble drug composition having improved absorbability of the fat-soluble component in the living body and being stable as a formulation, specifically a fat-soluble drug composition for capsules. The present invention relates to a fat-soluble drug composition comprising a fat-soluble component and an emulsifier, wherein the emulsifier contains diacetyltartaric and unsaturated fatty acid esters of glycerol and a glycerol ester of unsaturated fatty acid.

2 Claims, No Drawings

FAT-SOLUBLE DRUG COMPOSITION

BACKGROUND OF THE INVENTION

1. Field of the Invention

The present invention relates to a fat-soluble drug composition comprising a fat-soluble component and an emulsifier, specifically a fat-soluble drug composition for capsules.

2. Description of the Related Art

Conventionally, use of soft capsules comprising a fat-soluble component raised problems of low absorption rate in the living body, e.g., in the stomach, intestine, etc., and slow absorption rate. To solve such problems, self-emulsifying type fat and oil compositions comprising a polyglycerol fatty acid ester are known (see Japanese Examined Patent Publication (JP-B) No. 4-74339 and Japanese Patent Application Laid-open (JP-A) No. 61-12632). However, those compositions do not have sufficient self-emulsifying property. Furthermore, they have a problem of high viscosity, which makes handling of them difficult.

Moreover, there are known methods which comprises filling a soft capsule with a self-emulsifying type fat and oil composition containing polyglycerol condensed-ricinoleic acid ester and polyglycerol laurate as emulsifiers (see JP-A No. 2004-115544 and JP-A No. 2004-135681). However, the content percentages of the polyglycerol condensed-ricinoleic acid ester in those compositions are high, i.e., in the range of 15 to 60 wt %, which causes a problem of decreased content of the fat-soluble components in the soft capsule. Furthermore, where the content of the emulsifier in the soft capsule increases, the taste becomes bad when the soft capsule is used as an oral chewable-type capsule, etc., resulting in causing unpleasant feeling.

SUMMARY OF THE INVENTION

The object of the present invention is to provide a fat-soluble drug composition having improved absorbability of the fat-soluble component in the living body and being stable as a formulation, specifically a fat-soluble drug composition for capsules.

The inventors of the present invention have done intensive studies on the above-mentioned problems and found that such problems can be solved by incorporating diacetyltartaric and unsaturated fatty acid esters of glycerol, and a glycerol ester of unsaturated fatty acid in a fat-soluble component. Furthermore, the inventors have found that the above-mentioned problems can be solved more effectively by adjusting the incorporation ratio of the diacetyltartaric and unsaturated fatty acid esters of glycerol and the glycerol ester of unsaturated fatty acid, the content percentage of the diacetyltartaric and unsaturated fatty acid esters of glycerol and the glycerol ester of unsaturated fatty acid contained in the fat-soluble component, and the HLB value of the diacetyltartaric and unsaturated fatty acid esters of glycerol and that of the glycerol ester of unsaturated fatty acid, to specific values. Based on these findings, the inventors of the present invention have completed the present invention.

Namely, the present invention provides
(1) a fat-soluble drug composition comprising a fat-soluble component and an emulsifier, wherein the emulsifier contains diacetyltartaric and unsaturated fatty acid esters of glycerol and a glycerol ester of unsaturated fatty acid;
(2) the fat-soluble drug composition according to the above (1), wherein the ratio of the diacetyltartaric and unsaturated fatty acid esters of glycerol to the glycerol ester of unsaturated fatty acid contained in the fat-soluble drug composition is 1:4 to 4:1 (parts by mass);
(3) the fat-soluble drug composition according to the above (1) or (2), wherein the content percentage of the total of the diacetyltartaric and unsaturated fatty acid esters of glycerol and the glycerol ester of unsaturated fatty acid contained in the fat-soluble drug composition is 1 to 6 mass %;
(4) the fat-soluble drug composition according to any one of the above (1) to (3), wherein the diacetyltartaric and unsaturated fatty acid esters of glycerol has an HLB value of not less than 6 and the glycerol ester of unsaturated fatty acid has an HLB value of less than 6;
(5) the fat-soluble drug composition according to any one of (1) to (4), wherein the diacetyltartaric and unsaturated fatty acid esters of glycerol is diacetyltartaric and oleic acid esters of glycerol;
(6) the fat-soluble drug composition according to any one of the above (1) to (5), wherein the glycerol ester of unsaturated fatty acid is glycerol monooleate; and
(7) a soft capsule comprising the fat-soluble drug composition according to any one of the above (1) to (6).

Since the fat-soluble drug composition according to the present invention can disperse a fat-soluble component quickly and sufficiently in an aqueous solution, it can increase the amount and rate of absorption in the body, e.g., in the intestine.

Furthermore, the fat-soluble drug composition according to the present invention have excellent ability to decrease the surface tension of the emulsifier to be used, and can thus decrease the content of the emulsifier in the composition and increase the content of the fat-soluble component. Therefore, for example, where the fat-soluble drug composition according to the present invention is enclosed in a capsule, the amount of the emulsifier can be decreased, as mentioned above, even if the amount of the fat-soluble drug composition to be enclosed is smaller than that of a conventional self-emulsifying type fat and oil composition. Therefore, a fat-soluble drug composition comprising a sufficient amount of fat-soluble component (e.g., a fat-soluble drug) can be enclosed in a capsule.

Moreover, since the fat-soluble drug composition according to the present invention can prevent crystallization and precipitation of the emulsifier due to change with time and environment in the fat-soluble drug composition, for example, a capsule preparation being stable in the formulation can be provided.

In addition, since the content of the emulsifier is small, the taste and flavor during eating are fine and are not deteriorated by the emulsifier.

DETAILED DESCRIPTION OF THE PREFERRED EXAMPLES

The fat-soluble component used for the present invention is not specifically limited so long as it is lipophilic, and examples thereof include edible oils, lipophilic medicaments or foods, fragrances, fat-soluble pigments, etc. Examples of the edible oils include rapeseed oil, soybean oil, safflower oil, sunflower oil, rice bran oil, corn oil, cottonseed oil, sesame oil, wheat germ oil, evening primrose oil, perilla oil, etc.

Examples of the lipophilic medicaments or foods include fat-soluble vitamins (e.g., vitamin A, vitamin D, vitamin E, vitamin K, etc.), fat-soluble vitamin C derivatives (e.g., ascorbyl tetrahexyldecanoate), coenzyme Q10 (also referred to as ubiquinone or vitamin Q), docosahexaenoic acid (DHA), eicosapentaenoic acid (EPA), conjugated linoleic acid (CLA)

triglyceride, CLA, squalene, γ-linolenic acid, α-linolenic acid, medium-chain fatty acid triglyceride (MCT), etc., and fats and oils comprising them, etc. Preferable examples of fragrances include essential oils from natural flowers, woods, fruits, etc. approved as medicament additives or food additives, etc. These fat-soluble components may be used solely or in combination with two or more kinds thereof.

The emulsifier used in the present invention includes at least diacetyltartaric and unsaturated fatty acid esters of glycerol and a glycerol ester of unsaturated fatty acid, and may include other emulsifiers if desired.

Although the diacetyltartaric and unsaturated fatty acid esters of glycerol used for the present invention is not specifically limited, those having an HLB of not less than 6 are preferable.

The diacetyltartaric and unsaturated fatty acid esters of glycerol can be generally obtained by reacting a glycerol ester of unsaturated fatty acid and diacetyltartaric anhydride according to a known method (e.g., esterification reaction, etc.). The unsaturated fatty acid that constitutes the diacetyltartaric and unsaturated fatty acid esters of glycerol is not specifically limited so long as it is an unsaturated fatty acid derived from edible animal or vegetable fats and oils, and examples thereof may include a straight chain unsaturated fatty acid having 6 to 24 carbon atoms, preferably a straight chain unsaturated fatty acid having 8 to 18 carbon atoms, and more preferably a straight chain unsaturated fatty acid having 18 carbon atoms. Specific examples thereof include one or two or more kinds of unsaturated fatty acids selected from the group consisting of oleic acid, linoleic acid, linolenic acid, etc., and preferable examples thereof include an unsaturated fatty acid and a mixture thereof, containing oleic acid in an amount of about not less than 50 mass %, more preferably about not less than 70 mass %.

The glycerol ester of unsaturated fatty acid used for the present invention is not specifically limited, and examples thereof include monoglyceride of unsaturated fatty acid (e.g., glycerol monooleate, etc.), acetic and unsaturated fatty acid esters of glycerol, lactic and unsaturated fatty acid esters of glycerol, citric and unsaturated fatty acid esters of glycerol, succinic and unsaturated fatty acid esters of glycerol, etc.

The above-mentioned glycerol esters of unsaturated fatty acid can be used solely or as a combination of two or more kinds.

Although the unsaturated fatty acid that constitutes the glycerol ester of unsaturated fatty acid is not specifically limited, examples thereof include unsaturated fatty acids having 16 to 22 carbon atoms, preferably oleic acid, linoleic acid, linolenic acid, elaidic acid, erucic acid, etc.

The glycerol ester of unsaturated fatty acid used for the present invention can be produced according to a method known per se. For example, the glycerol ester of unsaturated fatty acid can be produced by charging glycerol and an unsaturated fatty acid in a molar ratio of about 1:0.8 to about 1:1.2, preferably about 1:1, in a general reaction vessel equipped with a stirrer, a jacket for heating, a baffle, etc., adding sodium hydroxide as a catalyst, mixing the mixture under stirring, and heating the mixture under nitrogen gas atmosphere and at a predetermined temperature while removing water generated during the esterification reaction from the system. The reaction temperature is generally in the range of about 180° C. to about 260° C., preferably in the range of about 200° C. to about 250° C. The pressure condition for the reaction is reduced pressure or atmospheric pressure, and the reaction time is about 0.5 hour to about 15 hours, preferably about 1 hour to about 3 hours. The end point of the reaction is generally determined by measuring the acid value of the reaction mixture and based on the acid value of about not more than 3. After the reaction is completed, the reaction solution is cooled to the temperature from about not less than 120° C. to about less than 180° C., preferably about 130° C. to about 150° C., the catalyst is neutralized by adding an acid, the mixture is preferably allowed to stand for about 15 minutes to about 1 hour, unreacted glycerol in the lower layer is removed if present, and the mixture is purified by molecular distillation using, for example, a falling film type molecular distillation apparatus or a centrifugation-type molecular distillation apparatus, or by a method known per se such as column chromatography, liquid-liquid extraction, etc., whereby a glycerol ester of unsaturated fatty acid can be obtained.

The fat-soluble drug composition according to the present invention preferably comprises the diacetyltartaric and unsaturated fatty acid esters of glycerol and the glycerol ester of unsaturated fatty acid in the ratio of about 1:4 to about 4:1 (parts by mass). This is because where the content ratio of the glycerol ester of unsaturated fatty acid relative to 1 part by mass of the diacetyltartaric and unsaturated fatty acid esters of glycerol in the fat-soluble drug composition is less than 0.25 parts by mass, the dispersibility of the fat-soluble component in an aqueous solution becomes bad, and where the content percentage exceeds 4 parts by mass, the emulsifier is precipitated.

The fat-soluble drug composition according to the present invention contains the diacetyltartaric and unsaturated fatty acid esters of glycerol and the glycerol ester of unsaturated fatty acid in the content percentage of about 1 mass % to about 6 mass %, preferably about 1 mass % to about 3 mass % in total relative to the fat-soluble drug composition. Where the content is less than 1 mass %, the self-emulsifying ability of the fat-soluble drug composition is decreased. Namely, the water dispersibility of the fat-soluble component in the aqueous solution is decreased, or the fat-soluble component is not dispersed in an aqueous solution.

The above-mentioned term "self-emulsifying ability" refers to an ability of dispersing (emulsifying) of the fat-soluble component in an aqueous solution wherein a solution of the emulsifier in the fat-soluble component, in which the emulsifier has been dissolved in the fat-soluble component in advance, is added dropwise to water without stirring.

Examples of the indices for representing self-emulsifying ability (water dispersibility of the fat-soluble component in water) include average particle size, etc. The average particle size can be measured by, for example, laser diffraction scattering method, dynamic light scattering method, image processing, etc. The fat-soluble drug composition according to the present invention preferably has an average particle size of about not more than 10 μm of the fat-soluble component measured by one of the above-mentioned three methods during dispersing of the fat-soluble drug composition in an aqueous solution.

The emulsifier used for the fat-soluble drug composition according to the present invention is preferably a combination of diacetyltartaric and unsaturated fatty acid esters of glycerol having an HLB value of not less than 6 and a glycerol ester of unsaturated fatty acid having an HLB of less than 6. Where the above-mentioned combination of the emulsifiers is contained in the fat-soluble drug composition, the water dispersibility of the fat-soluble component in the composition is remarkably improved. A fat-soluble drug composition containing only an emulsifier having an HLB of less than 6 does not have a problem in solubility of the emulsifier to the fat-soluble component, but has a problem in that the fat-soluble component is not dissolved in water. On the other hand, a fat-soluble drug composition containing only an emulsifier having an HLB of not less than 6 has a problem in that the emulsifier is difficult to dissolve in the fat-soluble component and is precipitated, and even if the emulsifier can be dissolved in the fat-soluble component, the fat-soluble component is not finely dispersed in the aqueous solution and the average particle size of the fat-soluble component does not become fine when the fat-soluble drug composition is contacted with the aqueous solution.

The HLB value (Hydrophile Lipophile Balance) refers to a value showing hydrophilicity of a surfactant. This is an index representing the balance of the lipophilicity and hydrophilicity of the object compound, which is determined as a relative value to an HLB value for a hypothetical compound, generally an ethylene oxide adduct-type nonionic surfactant having an infinite long hydrophilic group attached to a lipophilic group and having the maximum hydrophilicity, which is set to 20, and to an HLB value for a lipophilic compound having no hydrophilic group, which is set to 0.

The fat-soluble drug composition according to the present invention can be produced by dissolving the above-mentioned emulsifier in the fat-soluble component. During the dissolution, it is preferable to heat the mixture to about 60° C. to about 80° C. and stir the mixture using, for example, a stirrer having a coil, a jacket, a baffle, etc. for heating, which is used for general stirring. The shape of the stirring paddle used for the stirrer may be any of paddle-cross type, propeller type, fan turbine type, etc.

Examples of other emulsifiers that can be used for the present invention include polyglycerol condensed-ricinoleic acid ester, polyglycerol fatty acid ester, sucrose fatty acid ester, lecithin, polyoxyethylene sorbitan ester, etc.

Where necessary, antioxidants such as dibutylhydroxytoluene, dibutylhydroxyanisole or vitamin C palmitate, or preservatives such as propionic acid, etc. can be added to the fat-soluble drug composition according to the present invention.

The fat-soluble drug composition according to the present invention is preferably formulated into a capsule preparation and used for medicaments, foods, etc. Either a hard capsule or a soft capsule may be preferably used for the capsule preparation.

More preferably, the hard capsule is one capable of preventing leaking of the fat-soluble drug composition filled in the capsule, for example, a hard capsule having a capsule body and a cap that have been integrated.

Examples of the soft capsule to be used may include conventional soft capsule base materials, e.g., soft capsule coatings prepared by appropriately mixing one or two or more kinds of gelatin, water-soluble polymers (e.g., agar, callagenane, furcellaran, gellan gum, native gellan gum, starch, processed starch, guar gum, tara gum, locust bean gum, sodium alginate, tamarind gum, pectin, gum arabic, pullulan, soybean polysaccharides, cellulose derivatives, etc.), sugars (e.g., trehalose, erythritol, mannitol, xylitol, sucrose, sorbitol, maltose, etc.) and glycerol, etc., or soft capsule coatings as described in JP-A No. 2005-170929, JP-A No. 2005-170863, JP-A No. 2004-351007, JP-A No. 2004-167084, JP-A No. 2002-360665, JP-A No. 2001-247453, JP-A No. 11-001427, etc. Preferable examples of the soft capsule to be used may include enteric soft capsules coated with corn-derived native protein etc., chewable capsules with taste or flavor, ultrathin film soft capsules (JP-A No. 2001-288075), etc. Where necessary, preserving agents, coloring agents, opaque agents, flavor agents, taste masking agents, etc., can also be appropriately added to the capsule coating.

The soft capsule can be produced according to a conventional method for the production of soft capsules, for example, stamping method using a rotary-type full automatic soft capsule forming machine, plane plate method comprising placing the fat-soluble drug composition according to the present invention between two gelatin sheets and stamping by compressing from both surfaces using molds, or dropping method (for seamless capsules, etc.) using a double nozzle, etc., thereby to form capsules, which are then dried.

The form of packaging of the produced soft capsules may be a generally known form, and examples thereof include filling in a bottle, aluminum packaging, PTP, etc.

In addition, since the fat-soluble drug composition of the present invention is readily dispersed in water, it can be used for processed foods (e.g., dressing, etc.), milk drinks, health foods, etc. that are produced by dissolving or emulsifying a fat-soluble component in water.

Hereinafter the present invention is explained in more detail based on Examples and Comparative Examples, but they should not be construed to limit the present invention.

EXAMPLES

1. Preparation of Fat-Soluble Drug Compositions

The fat-soluble drug compositions of Examples 1 to 4 and Comparative Examples 1 to 6 were prepared.

Example 1

To conjugated linoleic acid (CLA) triglyceride (94 g) (trade name: Tonalin TG-80, manufactured by Cognis Inc.) were added glycerol monooleate (3 g) (trade name; Emulsy OL-100H, manufactured by Riken Vitamin Co., Ltd.) and diacetyltartaric acid esters of monoglycerides (DATEM) (3 g) (Panodan AB-100V, manufactured by Danisco), and the mixture was heated to 70° C. and dissolved by stirring with a stirrer to prepare a fat-soluble drug composition.

Example 2

A fat-soluble drug composition was prepared according to a similar manner to Example 1, except that medium-chain fatty acid triglyceride (MCT) (42 g) (trade name; Actor M-107FR, manufactured by Riken Vitamin Co., Ltd.) and vitamin E (54 g) (tradename; Riken E-oil 800, manufactured by Riken Vitamin Co., Ltd.) were used instead of conjugated linoleic acid (CLA) triglyceride (94 g), and glycerol monooleate (1 g) was used instead of glycerol monooleate (3 g).

Example 3

A fat-soluble drug composition was prepared according to a similar manner to Example 1, except that rapeseed oil (94 g) (trade name; Boso Oil and Fat Co., Ltd.) was used instead of conjugated linoleic acid (CLA) triglyceride (94 g).

Example 4

A fat-soluble drug composition was prepared according to a similar manner to Example 1, except that medium-chain fatty acid triglyceride (MCT) (85 g) and coenzyme Q10 (trade name; Bio-Q10, manufactured by Mitsubishi Gas Chemical Co., Inc.) (10 g) were used instead of conjugated linoleic acid (CLA) triglyceride (94 g), and glycerol monooleate (2 g) was used instead of glycerol monooleate (3 g).

Comparative Example 1

A fat-soluble drug composition was prepared according to a similar manner to Example 1, except that medium-chain fatty acid triglyceride (MCT) (97 g) was used instead of conjugated linoleic acid (CLA) triglyceride (94 g), and diacetyltartaric acid esters of monoglycerides (DATEM) (3 g) was used instead of glycerol monooleate (3 g) and diacetyltartaric acid esters of monoglycerides (DATEM) (3 g).

Comparative Example 2

A fat-soluble drug composition was prepared according to a similar manner to Example 1, except that rapeseed oil (97 g) was used instead of conjugated linoleic acid (CLA) triglyceride (94 g), and diglycerol monooleate (3 g) (trade name; Poem DO-100V, manufactured by Riken Vitamin Co., Ltd.) was used instead of glycerol monooleate (3 g) and diacetyltartaric acid esters of monoglycerides (DATEM) (3 g).

Comparative Example 3

A fat-soluble drug composition was prepared according to a similar manner to Example 1, except that rapeseed oil (94 g) was used instead of conjugated linoleic acid (CLA) triglyceride (94 g), and hexaglycerol condensed-ricinoleic acid ester (3 g) (trade name; Poem PR-300, manufactured by Riken Vitamin Co., Ltd.) and decaglycerol laurate (3 g) (trade name; SY Glystar ML 750, manufactured by Sakamoto Yakuhin Kogyo Co., Ltd.) were used instead of glycerol monooleate (3 g) and diacetyltartaric acid esters of monoglycerides (DATEM) (3 g).

Comparative Example 4

A fat-soluble drug composition was prepared according to a similar manner to Example 1, except that medium-chain fatty acid triglyceride (MCT) (94 g) was used instead of conjugated linoleic acid (CLA) triglyceride (94 g), and hexaglycerol condensed-ricinoleic acid ester (3 g) and decaglycerol laurate (3 g) were used instead of glycerol monooleate (3 g) and diacetyltartaric acid esters of monoglycerides (DATEM) (3 g).

Comparative Example 5

A fat-soluble drug composition was prepared according to a similar manner to Example 1, except that medium-chain fatty acid triglyceride (MCT) (95 g) was used instead of conjugated linoleic acid (CLA) triglyceride (94 g), and hexaglycerol condensed-ricinoleic acid ester (2 g) was used instead of glycerol monooleate (3 g).

Comparative Example 6

A fat-soluble drug composition was prepared according to a similar manner to Example 1, except that rapeseed oil (85 g) and coenzyme Q10 (10 g) were used instead of conjugated linoleic acid (CLA) triglyceride (94 g), and propylene glycol oleate (2 g) (trade name; Rikemal PO-100, manufactured by Riken Vitamin Co., Ltd.) was used instead of glycerol monooleate (3 g).

2. Measurement of Self-Emulsifying Ability and Average Particle Size for Fat-Soluble Drug Compositions The self-emulsifying ability and average particle size for the fat-soluble drug compositions were measured by adding fat-soluble drug compositions of Examples 1 to 4 and Comparative Examples 1 to 6 (each 1 g) to tap water (100 g). The average particle size was measured using an LA-950 Laser Scattering Particle Size Distribution Analyzer (manufactured by Horiba Ltd.) by laser diffraction method. The self-emulsifying ability was determined by visually observing the state of the liquid, and the result was symbolized based on the following criteria.

○: homogeneously clouded and being stable

Δ: once clouded and emulsified, but oil layer and water layer were separated with time X: not clouded, but oil layer and water layer were separated The results are shown in Table 1.

3. Measurement of Crystallinity for Fat-Soluble Drug Compositions

The fat-soluble drug compositions of Examples 1 to 4 and Comparative Examples 1 to 6 were stored in a thermostat at 20° C., respectively, and they were observed for 1 month to evaluate the crystallinity. Where the composition became clouded or precipitate formation was observed therein, the composition was confirmed to have crystallinity. The results are shown in Table 1.

TABLE 1

|  |  | HLB | Property | Example 1 | Example 2 | Example 3 | Example 4 |
| --- | --- | --- | --- | --- | --- | --- | --- |
| Fat and oil | Medium-chain fatty acid triglyceride (MCT) |  | Liquid |  | 42 |  | 85 |
|  | Rapeseed oil |  | Liquid |  |  | 94 |  |
|  | Mix tocopherol (vitamin E) |  | Viscous liquid |  | 54 |  |  |
|  | Conjugated linoleic acid (CLA) triglyceride |  |  | 94 |  |  |  |
|  | Coenzyme Q10 |  |  |  |  |  | 10 |
| Emulsifier | Hexaglycerol condensed-ricinoleic acid ester | 1.7 | Liquid |  |  |  |  |
|  | Glycerol oleate | 4.3 | Semi-solid | 3 | 1 | 3 | 2 |
|  | Decaglycerol monolaurate | 15.0 | Paste |  |  |  |  |
|  | Diglycerol monooleate | 7.4 | Paste |  |  |  |  |
|  | PG oleic acid ester | 3.4 | Paste |  |  |  |  |
|  | DATEM | 9.5 |  | 3 | 3 | 3 | 3 |
|  | Self-emulsifying ability |  |  | ○ | ○ | ○ | ○ |
|  | Average particle size (μm) |  |  | 6.5 | 4 | 2.6 | 2.8 |
|  | Crystallinity (20° C., 1 month) |  |  | Not observed | Not observed | Not observed | Not observed |

TABLE 1-continued

|  |  | Comparative Example 1 | Comparative Example 2 | Comparative Example 3 | Comparative Example 4 | Comparative Example 5 | Comparative Example 6 |
|---|---|---|---|---|---|---|---|
| Fat and oil | Medium-chain fatty acid triglyceride (MCT) | 97 |  |  | 94 | 95 |  |
|  | Rapeseed oil |  | 97 | 94 |  |  | 85 |
|  | Mix tocopherol (vitamin E) |  |  |  |  |  |  |
|  | Conjugated linoleic acid (CLA) triglyceride |  |  |  |  |  |  |
|  | Coenzyme Q10 |  |  |  |  |  | 10 |
| Emulsifier | Hexaglycerol condensed-ricinoleic acid ester |  |  | 3 | 3 | 2 |  |
|  | Glycerol oleate |  |  |  |  |  |  |
|  | Decaglycerol monolaurate |  |  | 3 | 3 |  |  |
|  | Diglycerol monooleate |  | 3 |  |  |  |  |
|  | PG oleic acid ester |  |  |  |  |  | 2 |
|  | DATEM | 3 |  |  |  | 3 | 3 |
|  | Self-emulsifying ability | X | X | X | X | X | X |
|  | Average particle size (μm) | — | — | — | — | — | — |
|  | Crystallinity (20° C., 1 month) | Not observed | Not observed | Observed | Observed | Not observed | Not observed |

DATEM: diacetyltartaric and oleic acid esters of glycerol (Panodan AB-100V)

DATEM: diacetyltartaric acid esters of monoglycerides (Panodan AB-100V)

4. Preparation of Soft Capsules

Gelatin (5 kg) was homogeneously dispersed by adding it in several small portions to purified water (4.6 kg) that was heated to 60 to 70° C., under stirring. Under stirring, the temperature of the dispersion was raised to 80 to 90° C. to dissolve the gelatin completely. After the gelatin was dissolved, concentrated glycerol (1.5 kg) was added thereto, and the mixture was mixed homogeneously. The mixture was then cooled down to room temperature under gentle stirring to prepare gelatin sheets. Two of the gelatin sheets were fed to a pair of rotation rollers having a capsule mold, the fat-soluble drug compositions of Examples 1 to 4 and Comparative Examples 1 to 6 were injected by 100 mg each and filled to form capsules subsequently, and the capsules were punched out to give soft capsules.

5. Evaluation of Taste and Flavor of Soft Capsules Comprising the Compositions of the Present Invention The taste and flavor were evaluated by ten panelists for the soft capsules comprising the fat-soluble drug compositions of Examples 1 to 4 and Comparative Examples 1 to 6 that were prepared according to the above-mentioned 4, according to the following evaluation criteria as shown in the following Table 2.

TABLE 2

| Evaluation items | Score | Evaluation criteria |
|---|---|---|
| Taste | 4 | Good |
|  | 3 | Slightly good |

TABLE 2-continued

| Evaluation items | Score | Evaluation criteria |
|---|---|---|
|  | 2 | Slightly bad |
|  | 1 | Bad |
| Flavor | 4 | Good |
|  | 3 | Slightly good |
|  | 2 | Slightly bad |
|  | 1 | Bad |

The results were obtained as average values of the scores evaluated by ten panelists, and symbolized according to the
⊚: Extremely good (average value is not less than 3.5)
○: Good (average values is 2.5 to 3.4)
Δ: Slightly bad (average value is 1.5 to 2.4)
X: Bad (average value is not more than 1.4)
The results are shown in Table 3.

TABLE 3

|  | Example 1 | Example 2 | Example 3 | Example 4 |
|---|---|---|---|---|
| Taste | ⊚ | ⊚ | ○ | ⊚ |
| Flavor | ○ | ⊚ | ⊚ | ⊚ |

Consequently, it was found that the soft capsules and flavor.

The fat-soluble drug composition according to the present invention is useful as a composition to be filled in capsules.

What is claimed is:

1. A fat-soluble drug composition contained in a soft capsule comprising (1) a fat-soluble vitamin or coenzyme Q10 and (2) at least two emulsifiers, wherein a first emulsifier is diacetyltartaric acid esters of monoglycerides containing oleic acid as a constituent fatty acid and a second emulsifier is glycerol monooleate, wherein the emulsifiers are dissolved in the fat-soluble vitamin or the coenzyme Q10.

2. The fat-soluble drug composition according to claim 1, having self-emulsifying ability.

* * * * *